United States Patent [19]

Cheeseman et al.

[11] Patent Number: 5,254,569

[45] Date of Patent: Oct. 19, 1993

[54] (AMIDOMETHYL)NITROGEN HETEROCYCLIC ANALGESICS

[75] Inventors: Robert S. Cheeseman, Phoenixville, Pa.; Hollis S. Kezar, III, Newark; Richard M. Scribner, Wilmington, both of Del.

[73] Assignee: The Du Pont Merck Pharmaceutical Company, Wilmington, Del.

[21] Appl. No.: 640,561

[22] Filed: Jan. 14, 1991

[51] Int. Cl.$^5$ .............. C07D 211/32; C07D 401/12; A61K 31/443

[52] U.S. Cl. .................... 514/331; 514/326; 546/210; 546/212; 546/213; 546/214; 546/233; 546/234

[58] Field of Search .............. 546/233, 234, 210, 212, 546/214, 213; 514/331, 326

[56] References Cited

U.S. PATENT DOCUMENTS

| | | | |
|---|---|---|---|
| 3,342,826 | 9/1967 | Miller et al. | 546/233 |
| 4,035,373 | 7/1977 | Roll | 514/935 |
| 4,942,169 | 7/1990 | Sugimoto | 546/233 |
| 5,098,915 | 3/1992 | Desai et al. | 546/212 |

Primary Examiner—C. Warren Ivy
Assistant Examiner—Celia Chang
Attorney, Agent, or Firm—Theresa M. Stevens-Smith; Raymond G. Arner; Margaret A. Horn

[57] ABSTRACT

This invention relates to (amidomethyl)nitrogen heterocyclic and pyrrolidine compounds, pharmaceutical compositions containing them, methods of using such compounds and processes for making such compounds.

42 Claims, No Drawings

(AMIDOMETHYL)NITROGEN HETEROCYCLIC ANALGESICS

FIELD OF THE INVENTION

This invention relates to (amidomethyl)nitrogen heterocyclic and pyrrolidine compounds, pharmaceutical compositions containing them and methods of using these compounds as analgesics, diuretics, anticonvulsants, anesthetics, antistroke agents, sedatives, cerebroprotective agents and in treating eating disorders. This invention further relates to methods of making the compounds of this invention.

BACKGROUND OF THE INVENTION

Studies of the binding properties of opioid drugs and peptides at specific sites in the brain and other organs have suggested the existence of several types of opioid receptors. In the central nervous system (CNS), good evidence has been demonstrated for at least three categories of opioid receptors: μ (mu), K (kappa) and δ (delta). Nalorphine, W. R. Martin, Pharmacol. Rev., 19, 463-521 (1967), and a series of benzomorphans, W. R. Martin, et al., J. Pharmacol. Exp. Ther., 197, 517-532 (1976), were reported to display unusual pharmacological properties dissimilar to morphine, yet blocked by selective opioid antagonists. The existence of multiple subtypes of opioid receptors is of considerable interest as it suggests the possibility of separating the desirable (analgesic and psychotherapeutic) and the undesirable (abuse potential) effects of opioids.

Compounds that are agonists for K receptors have shown strong analgesia without opioid side effects such as dependence liability, respiratory depression, and constipation. The prototype of such compounds is U-50,488,trans-3,4-dichloro-N-methyl-N-[2-(pyrrolidin-1-yl)cyclohexyl]benzeneacetamide, which is described in U.S. Pat. No. 4,115,435, and reported by P. F. Von-Voigtlander, et al., J. Pharmacol Exp. Ther., 224, 7 (1983). This compound is stated to exhibit analgesic actions in a variety of assays, such as thermal, pressure and irritant, in mice and rats.

Spirocyclic analogs of U-50,488 are disclosed U.S. Pat. Nos. 4,359,476, 4,360,531, and 4,438,130, as analgesic compounds having low physical dependence liability in humans. Examples of these derivatives are trans-3,4-dichloro-N-methyl-N-[7-pyrrolidin-1-yl)-1,4-dioxaspiro[4.5]dec-6-yl]benzeneacetamide; tra dichloro-N-methyl-N-[7-(pyrrolidin-1-yl)-1,4-dioxaspiro[4.5]dec-8-yl]benzeneacetamide; and (±)-(5 7-a,9β)-3,4-dichloro-N-methyl-N-[7-(pyrrolidin-1-yl)-1-oxaspiro[4.5]dec-8-yl]benzene Omega-(Hydroxy-, Ether and Ester)-Alkyl-2-Amino-cycloalkyl and Cycloalkenyl Amides active as analgesics are disclosed in U.S. Pat. No. 4,632,935.

Substituted trans-1,2-diaminocyclohexylamide compounds such as trans-N-methyl-N-[2-(1-pyrrolidinyl)-cyclohexylbenzo[b]thiophene-4-acetamide are disclosed in U.S. Pat. No. 4,656,182. Naphthalenyloxy-1,2-diaminocyclohexyl amide compounds active as analgesics are disclosed in U.S. Pat. No. 4,663,343.

Benzo-fused cycloalkene trans-1,2-diamine derivatives such as trans-3,4-dichloro-N-methyl-N-[2-(pyrrolidin-1-yl)-5-methoxy-1,2,3,4-tetrahydronapth-1yl]benzene acetamide hydrochloride are disclosed in U.S. Pat. No. 4,876,269.

Diamine compounds such as (2S)-N-[2-(N-methyl-3,4-dichlorophenylacetamide)-2-phenylethyl]pyrrolidine are described in European Patent Application 0254545.

1-Acyl-2-aminomethyl-saturated aza-heterocyclic compounds such as (2S)-1-Q-acetyl-2-(pyrrolidin-1-yl)-methylpiperidine, where Q is 1-oxa-3,4-dihydro-2 naphth-6-yl are disclosed in European Patent Application 333315.

None of the cited references describe the (amidomethyl)nitrogen heterocyclic compounds of the present invention.

SUMMARY OF THE INVENTION

There are described compounds of the formula:

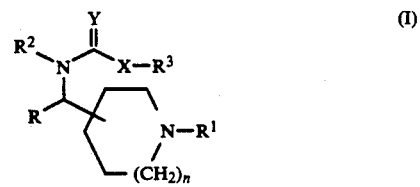

or a pharmaceutically acceptable salt or a stereoisomer thereof wherein:

R is C1-C10 alkyl, C6-C10 carbocyclic aryl, $(CH_2)_mOAr$, $(CH_2)_{mSAr}$ $(m=1-3)$, alkyl aryl or a heterocyclic aryl group each optionally substituted with one or more substituents independently selected from the group consisting of:

fluorine, chlorine, bromine, trifluoromethyl, cyano, nitro, hydroxy, thiol, trifluoromethylsulfonyl, 1,1,2,2-tetrafluoroethylsulfonyl, C1-C3 alkyl, C1-C3 alkoxy, haloalkyl of 1-3 carbon atoms and 1-7 halogen atoms, $CO_2H$, tetrazole, carboalkoxy of 2-6 carbon atoms, $S(O)_qR^4$ $(q=0-3)$, $NR^5R^6$, $COR^7$, $CONR^8R^9$ or $SO_2NR^8R^9$; $R^1$ is H, C1-C6 alkyl, C1-C6 alkenyl including branched chain alkenyl, C3-C6 cycloalkyl, C3-C6 cycloalkylmethyl, benzyl, phenethyl, or 3-phenylpropyl;

$R^2$ is C1-C3 alkyl;

$R^3$ is C6-C10 carbocyclic aryl or a heterocyclic aryl group each optionally substituted with one or more substituents independently selected from the group consisting of:

fluorine, chlorine, bromine, trifluoromethyl, cyano, nitro, hydroxy, thiol, trifluoromethylsulfonyl, 1,1,2,2-tetrafluoroethylsulfonyl, C1-C3 alkyl, C1-C3 alkoxy, $CO_2H$, tetrazole, carboalkoxy of 2-6 carbon atoms, $S(O)_qR^4$ $(q=0-3)$, $NR^5R^6$, $COR^7$, $CONR^8R^9$ or $SO_2NR^8R^9$;

$R^4$ to $R^9$ independently are H or C1-C6 alkyl;

X is single bond, $CH_2$, $CH_2O$, $CH_2S$ or $CH_2NH$;

Y is O or S;

n is 0-3; and

Ar and Ar' independently are C6-C10 carbocyclic, aryl or heterocyclic aryl, each optionally substituted with one or more subsituents independently selected from the group consisting of:

fluorine, chlorine, bromine, trifluoromethyl, cyano, nitro, hydroxy, thiol, trifluoromethylsulfonyl, 1,1,2,2-tetrafluoroethylsulfonyl, C1-C3 alkyl, C1-C3 alkoxy, $CO_2H$, tetrazole, carboalkoxy of 2-6 carbon atoms, $S(O)_qR^4$ $(q=0-3)$, $NR^5R^6$, $COR^7$, $CONR^8R^9$ or $SO_2NR^8R^9$.

The preferred compounds of this invention are the compounds of Formula (I) wherein:

R is aryl, 2-furanyl or 2-thienyl; and/or

X is CH₂, CH₂O, CH₂S, or CH₂NH; and/or
Y is O; and/or
n is 0 or 1; and/or
the piperidine ring is attached at the 2-position.

More preferred compounds are the RR and SS diastereomers of compounds in the preferred scope. Specifically preferred are the compounds of Formula (I) wherein:

R is phenyl or substituted phenyl; and/or
$R^1$ and $R^2$ are methyl; and/or
$R^3$ is 3,4-dichlorophenyl or 4-benzofuranyl; and/or
X is CH₂ or CH₂O; and/or
Y is O; and/or
n is 1; and/or
the piperidine ring is attached at the 2-position; and/or
SS diastereomer.

DETAILED DESCRIPTION OF THE INVENTION

SCHEME 1

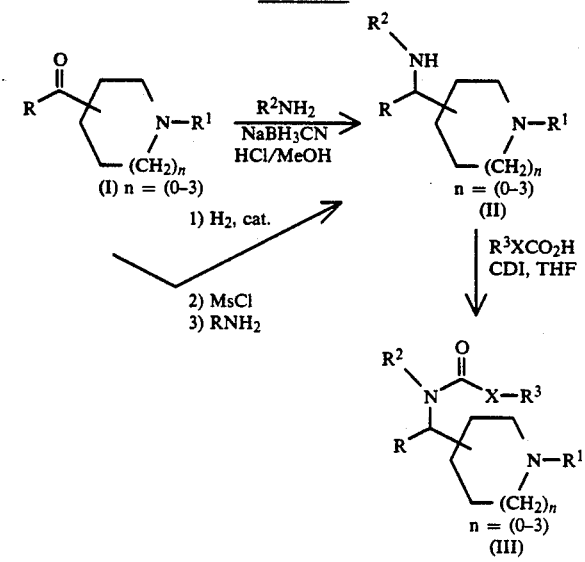

Methods for the synthesis of the Compounds of the invention are illustrated in Scheme 1.

The starting compounds of Formula (I) can be prepared according to literature procedures or by modifications to these procedures which should be apparent to those familiar with the art of organic synthesis.

A convenient way to prepare the starting ketone (I) employs an organometallic reactant such as magnesium or lithium with N-alkylcycloamine substituted with either nitrile, aldehyde or carboxy in the appropriate position. Other routes to starting ketone (I) utilize a Friedel-Crafts reaction of an N-alkylcycloamine acid chloride. The preferred time and temperature depend on the nature of R. References that describe the preparation of ketone (I) or their precursors include: Helv. Chim. Acta 1967, 50(8)2520-2531; J. Med. Chem. 11(3), 472-5 (1968); JOC 16, 1790 (1951); JACS 81, 1201 (1959); JOC 17, 249-252 (1952); U.S. Pat. No. 3,459,750; Zh. Org. Khimi, 9(11), 2245-51 (1973); Dokl. Akad. Nauk SSSR, 179(2), 345-348 (1968); J. Org. Chem., 39(7), 893-902 (1974).

According to Scheme 1, a ketone (I) can be converted into a diamine (II) by a primary amine such as propylamine and sodium cyanoborohydride in a polar solvent such as isopropanol in the presence of a stoichiometric amount of an inorganic acid at a temperature between about 0° and 70° C. with reaction times between about 1 and 48 hours. Alternatively, the diamine (II) can be prepared by converting a ketone (I) to its alcohol with hydrogen using a catalyst as known to those skilled in the art, such as platinum oxide or palladium on carbon in a polar solvent such as acetic acid or ethanol.

Conversion of the aminoalcohol to a diamine (II) can be done with methanesulfonyl chloride in the presence of a base such as triethylamine at a temperature between about 0° and 5° C. Further treatment of the resulting sulfonate with an excess of an alcoholic solution of an amine (RNH2) such as methylamine, ethylamine or n-propylamine, at a temperature between about 70° and 80° C. yields a diamine (II).

Alternatively, the aminoalcohol can be treated with chlorosulfonic acid in a chlorinated solvent such as methylene chloride at a temperature between about 0° and 25° C. to afford the sulfate salt which on treatment with an amine (RNH2) affords a diamine (II).

The diamine (II) is converted to (III) by conventional methods, e.g., treatment with a carboxylic acid ($R^3$XCOOH) either as its acid chloride in the presence of triethylamine, or aqueous sodium bicarbonate, or as its acyl imidazole prepared by reacting the acid with carbonyl diimidazole or with the acid itself in the presence of dicyclohexyl-carbodiimide. In Scheme 1, the end product (III) encompasses the compounds of this invention having the Formula (I) as described in the Summary of the Invention.

Additional methods for the synthesis of the compounds of the invention are illustrated in Scheme 2.

SCHEME 2

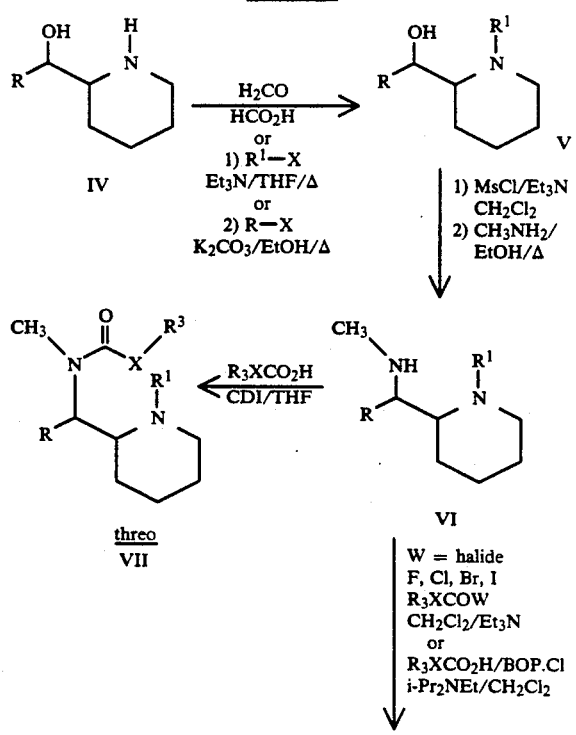

-continued
SCHEME 2

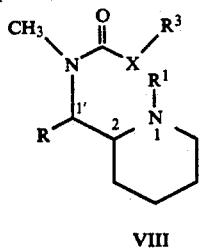

VIII

The starting compounds (IV) can be prepared enantiomerically either according to literature procedures or by modifications to these procedures which should be apparent to those familiar with the art of organic synthesis. References that describe the chiral preparation of (IV) include: *J. Org. Chem.*, 50, Q, 670 (1985); *Syn. Commun.*, 18, 823 (1988)

According to Scheme 2, compounds (IV) can be converted into a compound (V) when $R=CH_3$, by the addition of formaldehyde in water and formic acid at a temperature between about 70° and 100° C. Alternatively, the compounds (V) can be prepared by treating the compounds (IV) with a base such as triethylamine when using a solvent such as tetrahydrofuran or a base such as potassium carbonate when using a solvent such as ethanol and RX where X is a halogen such as bromine at reflux temperatures.

An aminoalcohol (V) is converted stereoselectively to a diamine (VI) by first reacting with methanesulfonyl chloride in a chlorinated solvent such as methylene chloride in the presence of a base such as triethylamine at a temperature between about 0° C. and room temperature. Further treatment of the resulting intermediate with an excess of an alcoholic solution of an amine such as methylamine at a temperature between about 70° and 80° C. yields a diamine (VI).

A diamine (VI) is converted to a compound (VIII) by conventional methods, e.g., treatment with a carboxylic acid ($ArYCO_2H$) either as its acid chloride in the presence of triethylamine, or as its activated ester prepared by reacting the acid with bis(2-oxo-3-oxazolidinyl)-phosphinic chloride, or in the R,R/S,S case, carbonyldiimidazole.

Scheme 1 outlines the most general route to the compounds of the invention. Those skilled in the art of organic synthesis will appreciate that to prepare compounds of Formula (I), (II) or (III) different starting materials may be preferable. For example it may be preferable to begin the reaction sequence from a starting material (a compound of Formula (I) or (II)) where R, $R^1$, $R^2$ groups are precursors to the eventually desired groups. Thus, R may be nitro or acetamido substituent and later in the sequence it may be reduced to $NH_2$ or $NHC_2H_5$. The sequence may also start from compounds of Formula I where R incorporates a methoxy substituent which is demethylated later, e.g., at the end of the sequence, to the corresponding phenol. It may be convenient to have R with a carboxylic ester substituent, e.g., a tertiary-butylcarboxylic ester, and then at the end of the synthesis, to hydrolyze and reduce the ester group to $CH_2OH$ or CHO; or to hydrolyze and react the ester group with an appropriate organometallic reagent such as methyl lithium to afford COR.

Pharmaceutically acceptable acid addition salts of amines (III) can be prepared by reacting the free base (III) with a stoichiometric amount of an appropriate acid such as hydrogen chloride, hydrogen bromide, hydrogen iodide, phosphoric acid, sulfuric acid, acetic acid, lactic acid, maleic acid, fumaric acid, succinic acid, citric acid, benzoic acid, salicyclic acid, pamoic acid, methanesulfonic acid, naphthalenesulfonic acid, p-toluenesulfonic acid and the like. The reaction can be carried out in water or in an organic solvent, or a mixture of the two; but nonaqueous media like ether, ethyl acetate, ethanol, isopropranol, or acetonitrile are generally preferred.

The invention can be further understood by the following examples in which parts and percentages are by weight unless otherwise indicated and all temperatures are in degrees centigrade. The compounds were analyzed by proton NMR, TLC, mass spectroscopy, and by elemental analysis (C, H, N).

EXAMPLE 1

Benzeneacetamide.
3,4-dichloro-N-methyl-N-1-(1-methyl-2-pyrrolidinyl)-1-phenylmethyl]-hydrochloride

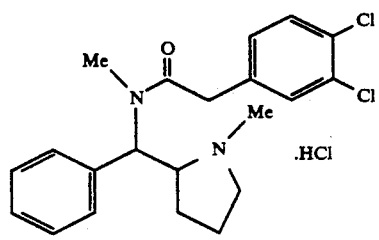

N-methyl-L-proline was prepared following a procedure given in Helv. Chim. Acta 1967, 50, 8, p. 2527. Collected 7.1 g white crystals (95% yield).

2-benzoyl-N-methylpyrrolidine was also prepared according to a method given in Helv. Chim. Acta 1967, 50, 8, p. 2527. Collected 5.5 g (37% yield) yellow crystals after recrystallization from hexane.

Methylamine (17.37 ml, 0.139 mol, 8.03 M in ethanol) and 3 N HCl in methanol (15.49 ml, 0.046 mol) were mixed in methanol (50 ml) under nitrogen. The ketone (4.4 g, 0.023 mol) was added in one portion and stirred several minutes before adding sodium cyanoborohydride (0.92 g, 0.0139 mol). Stirring was continued overnight at room temperature. The reaction mixture was acidified to pH 2 using 12 N HCl. The solvent was removed using a rotary evaporator, herein referred to as "rotovap" (commercially available from Buchi) leaving a residue which was dissolved in water (50 ml). This aqueous solution was treated with ether (3×50 ml). The aqueous layer was basified using solid potassium hydroxide to pH 10. This basic solution was extracted with ether (3×50 ml). The combined organic extracts were dried over anhydrous magnesium sulfate, filtered and stripped leaving 4.5 g (95% yield) yellow oil of the diamine.

Carbonyldiimidazole (2.07 g, 0.0127 mol) and 3,4-dichlorophenylacetic acid (4.04 g, 0.0197 mol) were dissolved in tetrahydrofuran (150 ml) under nitrogen at about 0° C. and stirred for one hour. The diamine in tetrahydrofuran (50 ml) was added dropwise. After addition was complete, the reaction mixture was stirred overnight at room temperature. The solvent was removed using a rotavap. The oily residue was partitioned between ethyl acetate (150 ml) and 10% potassium carbonate (75 ml). The organic layer was separated and dried over potassium carbonate. After filtering, the solvent was removed leaving 7.1 g tan oil. This material was purified using flash chromatography (eluent:ethyl acetate with 1% dimethylethylamine). Collected 2.6 g (44% yield) tan oil of the amide. This material was dissolved in ether (50 ml) and treated with 1M HCl in ether (10 ml). Collected 2.6 g light yellow solid which was recrystallized in isopropanol/ether. Obtained crystals which were dried under vacuum at about 78° C. Collected 1.1 g (39% yield) off-white crystals of benzeneacetamide, 3,4-dichloro-N-methyl-N-[(1-methyl-2-pyrrolidinyl)-1-phenylmethyl)]-, hydrochloride mp 205°-209° C.

Anal. Calcd. for $C_{21}H_{24}Cl_2N_2O \cdot HCl \cdot \frac{1}{4}H_2O$: C, 58.35. H, 5.95. N, 6.48. Found: C, 58.50. H, 6.13. N, 6.28.

EXAMPLE 2

Benzeneacetamide, 3,4-dichloro-N-methyl-N-((1-(1-methyl-2-piperidinyl) phenylmethyl))-, hydrochloride

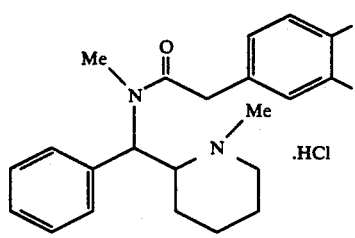

Methyl trifluoromethanesulfonate (10 ml, 0.088 mol) was added in one portion to 2-benzoylpyridine (16.3 g, 0.089 mol) in ether (500 ml) while cooling in an ice bath. Stirring was continued (15 hours) as the reaction warmed to ambient temperature. A white precipitate formed. This material was collected and washed with fresh ether. Collected 29.9 g (98% yield) white solid.

The trifluoromethanesulfonate salt of N-methyl-2-benzoylpyridine (23.2 g, 0.066 mol) was added to a Parr bottle containing platinum oxide (0.20 g) and acetic acid (100 ml). Hydrogenation was stopped after 8 hours and a 299 psi drop in pressure. The reaction mixture was filtered. The filtrate was concentrated using a rotovap and poured onto ice. It was basified using 25% sodium hydroxide to pH 11. This aqueous mixture was extracted with ethyl acetate. The organic layer was washed with a small amount of water and brine. It was dried over potassium carbonate, filtered and stripped. The residue was dissolved in toluene and filtered. The toluene was stripped using the rotovap leaving 12.1 g (88% yield) 2-(α-hydroxybenzyl)-N-methylpiperidine.

The aminoalcohol (12.1 g, 0.059 m) and triethylamine (10 ml, 0.072 mol) were dissolved in methylene chloride (200 ml) under nitrogen and cooled in an ice bath. Methanesulfonyl chloride (7.43 g, 1.1 eqv.) in methylene chloride (30 ml) was added dropwise over 25 minutes. The reaction mixture was stirred an additional 1.5 hours before the solvent was removed using a rotovap (bath temp. 35° C.). The residue was transferred to a Parr bottle containing methylamine (35 ml, 8M in ethanol). Additional ethanol (25 ml) was used to complete the transfer. The Parr bottle was sealed and heated at 80° C. for 24 hours. The reaction solvent was stripped and 10% potassium carbonate was added to the residue. This aqueous mixture was extracted with ethyl acetate (2×). The combined organic layers were dried over potassium carbonate/sodium sulfate, filtered and stripped leaving 12.5 g (97% yield) liquid diamine.

Carbonyldiimidazole (11.2 g, 0.068 mol) in methylene chloride (125 ml) was added dropwise over 15 minutes to a solution of 3,4-dichlorophenylacetic acid (14.1 g, 0.068 mol) in methylene chloride (100 ml) under nitrogen. After stirring at room temperature for 3 hours, the diamine (12.5 g, 0.057 mol) was added. The reaction mixture was stirred 27 hours and extracted with 10% potassium carbonate. The organic layer was dried over potassium carbonate/sodium sulfate, filtered and stripped leaving 27.4 g oil. This material was treated with ethyl acetate (20 ml) to give a white solid which was collected and washed with fresh ethyl acetate followed by diethyl ether. The crude white solid was recrystallized in ethyl acetate which after drying under vacuum at 78° C. gave 6.33 g (27% yield) white crystals of the amide. This amide (5 g) was suspended in tetrahydrofuran (50 ml) and 1 M HCl in ether (13 ml) was added. After stirring briefly, the solvent was removed using a rotovap. The residue was treated with hot acetone (100 ml) and cooled. A white solid was isolated and dried under vacuum at about 78° C. Collected 5.2 g (95% yield) white powder of benzeneacetamide, 3,4-dichloro-N-methyl-N-[1-(1-methyl-2-piperidinyl)phenyl-methyl], hydrochloride.

Anal. Calcd. for $C_{22}H_{26}N_2OCl_2 \cdot HCl \cdot 0.75H_2O$: C, 58.03. H, 6.31. N, 6.15. Found: C, 58.02. H, 6.12. N, 5.99.

EXAMPLE 3

Benzeneacetamide, 3,4-dichloro-N-[(1-((1-cyclopropylmethyl)-2-piperidinyl))-1-phenylmethyl)]-N-methyl-, hydrochloride

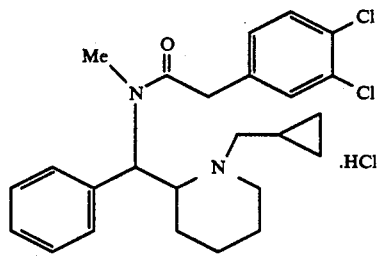

2-(α-hydroxybenzyl)piperidine was prepared using the procedure given in U.S. Pat. No. 3,459,750. m.p. 138.3°-138.7° C. Prepared 38.0 g (39% yield).

(Bromoethyl)cyclopropane (5.0 g, 0.037 mol) was added dropwise to a solution of the piperidinylalcohol (7.7 g, 0.04 mol) and sodium carbonate (5.0 g, 0.047 mol) in dimethylformamide (25 ml) and water (3 ml). The reaction mixture was stirred at room temperature for 0.5 hours and then at 60° C. for 1.5 hours. The reaction mixture was cooled and mixed with water (200 ml). This aqueous mixture was extracted with ether (200 ml). The organic layer was treated with water (2×) and brine. The organic layer was dried over potassium carbonate, filtered and stripped. The residue was treated with 5% HCl (100 ml) and extracted with ether. The aqueous layer was basified using potassium carbonate and extracted with ether. The ether layer was dried over potassium carbonate, filtered and stripped leaving 6.7 g (71% yield) clear liquid.

2-(α-hydroxybenzyl)-N-cyclopropylmethylpiperidine (2.45 g, 0.010 mol) was dissolved in methylene chloride (200 ml) under nitrogen and cooled to about 0° C. Triethylamine (2.2 ml, 0.0158 mol) was added followed by the dropwise addition of methanesulfonyl chloride (1.48 g, 0.0129 mol) in methylene chloride (3 ml). The reaction mixture was stirred overnight as it slowly reached ambient temperature. The solvent was removed using a rotovap and the residue was treated with methylamine (9 ml, 0.070 mol, 8 M in ethanol) in a sealed flask at about 70° C. for about 24 hours. The reaction mixture was cooled and partitioned between 20% potassium carbonate and ethyl acetate. The organic layer was dried over potassium carbonate, filtered and stripped leaving 3.5 g semi-solid. This material was treated with ether (20 ml) and filtered. The solvent was removed leaving 2.3 g (89% yield) waxy semi-solid diamine.

Carbonyldiimidazole (1.63 g, 0.010 mol) and 3,4-dichlorophenylacetic acid (2.05 g, 0.009 mol) were dissolved in methylene chloride(75 ml) and stirred for 2 hours at room temperature. The diamine (2.0 g, 0.0077 mol) was added to this mixture and stirring was continued overnight at room temperature. The reaction mixture was stripped and the residue was partitioned between 10% potassium carbonate and ethyl acetate. The organic layer was dried over potassium carbonate, filtered and stripped leaving 3.4 g amber residue. This material was purified using flash chromatography (eluent:ethyl acetate/hexane (1:1) with 1% dimethylethylamine). Collected 930 mg solid which was dissolved in warm ether (50 ml), filtered, and concentrated. White crystals formed upon cooling. Collected 260 mg (7.5% yield) white solid of the desired amide.

The amide (225 mg) was dissolved in warm anhydrous ether (50 ml) and 1 N HCl in ether (0.6 ml) was added. The reaction mixture was stirred 0.5 hours and a white solid was collected. This material was dried under vacuum at about 78° C. giving 188 mg (77% yield) white powder of benzeneacetamide,3,4-dichloro-N-[1-(1-cyclopropylmethyl)-2-piperidinyl-I-phenylmethyl]-N-methyl-,hydrochloride. High resolution mass spectrum agreed with expected product.

EXAMPLE 4

Benzeneacetamide, 3,4-dichloro-N-methyl-n-((1-(1-methyl-2-piperidinyl) ethyl))-, hydorchloride

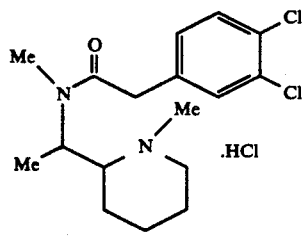

2-acetylpyridine (24.2 g, 0.20 mol), methylamine hydrochloride (27 g, 0.40 mol) and methylamine (26 ml, 0.21 mol, 8M in ethanol) were dissolved in methanol (200 ml) in a sealed flask and stirred several minutes at room temperature. The reaction flask was cooled in an ice bath and sodium cyanoborohydride (12.6 g, 0.20 mol) was added in portions. Stirring was continued for 1.5 hours at ice bath temperature.

The cooling bath was removed and stirring was continued for 66 hours. The reaction solvent was removed using a rotovap and the residue was stirred with water (50 ml) and methylene chloride (350 ml). Potassium carbonate was added until the aqueous layer was absorbed. The organic layer was decanted and the solid was washed with fresh methylene chloride (300 ml). The combined organic layers were stripped giving 29.6 g light purple oil. A bulb to bulb distillation (85°–95° C., 15 mm) gave 17.4 g colorless liquid amine (64% yield).

Carbonyldiimidazole (8.6 g, 0.053 mol) and 3,4-dichlorophenylacetic acid (10.76 g, 0.053 mol) were dissolved in methylene chloride (25 ml) and stirred at room temperature for about 2 hours. The amine (4.75 g, 0.035 mol) was added to the reaction mixture and stirring was continued for about 20 hours. The reaction solvent was removed using a rotovap leaving a brown oil which was dissolved in 5% hydrochloric acid. This aqueous layer was washed with diethyl ether (2×), basified using potassium bicarbonate and extracted with diethyl ether (2×). The combined ether layers were dried over potassium carbonate, filtered and stripped leaving 8.8 g (78% yield) oil of the expected amide.

The amide (5.88 g, 0.0182 mol) was dissolved in diethyl ether (100 ml) under nitrogen and cooled in an ice bath. Methyl trifluoromethanesulfonate (3.3 g, 0.020 mol) was added dropwise. The reaction mixture was stirred 96 hours at room temperature. A white solid was collected and washed with fresh diethyl ether giving 9 g (100% yield) of the pyridine salt.

The pyridine salt (9 g, 0.0182 mol) was dissolved in acetic acid (75 ml) and trifluoroacetic acid (2 ml). Platinum oxide (0.20 g) was added and hydrogenation was initiated. After 6 hours and a 68 psi drop in hydrogen pressure, the reaction solvent was removed and the residue was partitioned between 20% potassium carbonate and methylene chloride. The organic layer was dried over potassium carbonate, filtered and stripped leaving a residue which was purified using flash chromatography (eluent: ethyl acetate with 1% dimethylethylamine). Collected 2.6 g (42% yield) of the expected product.

The amide was dissolved in diethyl ether (100 ml) and treated with 1 N HCl in ether. After stirring 2 hours, a white solid was collected. This material was recrystallized in acetonitrile/ethyl acetate to give 1.06 g (37% yield) white crystals of benzeneacetamide,3,4-dichloro-N-methyl-N-[1-(1-methyl-2-piperidinyl)ethyl]-, hydrochloride. mp.185°–187

Anal. Calcd. for C17H24C12N20.HCl: c, 53.77. H, 6.64. N, 7.38. Found: C, 53.69. H, 6.69. N, 7.29.

EXAMPLE 5

Benzeneacetamide,3,4-dichloro-N-((1-(3-methoxyohenyl)-1-(1-methyl-2-piperidinyl)methyl))-N-methyl-, hydrochloride

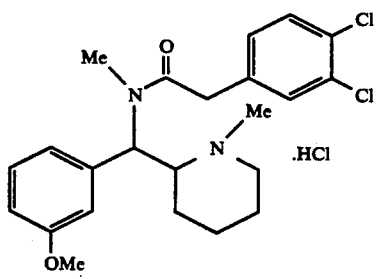

3-Bromoanisole (41.1 g, 0.22 mol) and magnesium (6.1 g, 0.25 mol) were reacted in diethyl ether (600 ml) under nitrogen. The reaction mixture was refluxed 0.5 hour and stirred at room temperature for 18 hours. 2-Cyanopyridine (22.8 g, 0.22 mol) in diethyl ether (75 ml) was added dropwise while gently refluxing the reaction mixture. After addition was complete, refluxing was continued for 4 hours. The reaction mixture was stirred at room temperature for 65 hours and poured onto crushed ice (1 liter) containing conc. sulfuric acid (50 ml, 0.90 mol). This mixture was shaken in a separatory funnel. The ether layer was removed and the aqueous layer was washed with fresh ether. The aqueous layer was heated on the steam bath (1 hour) cooled and basified to pH 9-10 using 25% sodium hydroxide. This basic mixture was extracted with diethyl ether (2×). The combined organic layers were dried over potassium carbonate, filtered and stripped leaving 21.4 g dark oil. This material was combined with crude product from a another run and purified using bulb to bulb distillation (120°-130° C., 0.4 mm). Collected 32.2 g (69% yield) yellow oil of the ketone.

The ketone (13.6 g, 0.064 mol) was dissolved in diethyl ether (300 ml) under nitrogen and cooled in an ice bath. Methyl trifluoromethanesulfonate (10 g, 0.061 mol) was added dropwise. After addition was complete, stirring was continued 18 hours as the reaction mixture reached ambient temperature. A white solid precipitate was collected, washed with fresh ether and dried under nitrogen.

The triflate salt of the ketone was dissolved in glacial acetic acid (10 ml) and platinum oxide (350 mg) was added. This mixture was hydrogenated (5.5 hours) on a Parr shaker. The solvent was removed using a rotovap and the residue was partitioned between water and methylene chloride. An excess of potassium carbonate was added and the organic layer was separated. The organic layer was dried over potassium carbonate, filtered and stripped leaving 14.5 g yellow oil. This oil was a mixture of the desired aminoalcohol and the partially reduced aminoketone. This material was dissolved in ethanol (100 ml) and sodium borohydride (1.5 g, 0.0375 mol) was added in portions. After stirring 2 hours at room temperature, additional sodium borohydride (1.0 g) was added to the reaction mixture and stirring continued for 2 hours. The solvent was removed using a rotovap and the residue was partitioned between 10% sodium carbonate and methylene chloride. The organic layer was dried over potassium carbonate, filtered and stripped leaving 13.0 g (86% yield) liquid.

The aminoalcohol (13.0 g, 0.0553 mol) and triethylamine (6.7 g, 0.0664 mol) were dissolved in methylene chloride (100 ml) under nitrogen and cooled in an ice bath. Methanesulfonyl chloride (7.0 g, 0.061 mol) in methylene chloride (30 ml) was added dropwise. Stirring was continued for 2 hours and the solvent was removed using a rotovap (bath temp. 35° C.). The residue was dissolved in ethanol (50 ml) and treated with methylamine (50 ml, 8M in ethanol) in a sealed flask at 80° C. for 40 hours. The reaction solvent was removed and the residue was mixed with water, treated with excess potassium carbonate and extracted with methylene chloride (2×). The combined organic layers were dried over potassium carbonate, filtered and stripped leaving 12.5 g (91% yield) liquid diamine. Residual water was removed by dissolving the product in toluene and removing this solvent using a rotovap.

Carbonyldiimidazole (10.0 g, 0.0617 mol) in methylene chloride (125 ml) was added dropwise to a solution of 3,4-dichlorophenylacetic acid (12.6 g, 0.0617 mol) in methylene chloride (100 ml) under nitrogen. After stirring for 4 hours at room temperature, the diamine (12.5 g, 0.050 mol) in methylene chloride (50 ml) was added to the reaction mixture. The reaction was stirred 120 hours at room temperature and then refluxed 2.5 hours. The reaction mixture was washed with 10% potassium carbonate (2×) and brine (1×). The organic layer was dried over potassium carbonate, filtered and stripped leaving 21.4 g amber oil. This oil was purified using flash chromatography (eluent: ethyl acetate/methanol, 95:5 with 1% dimethylethylamine). Collected 7.2 g (33% yield) oil. This amide was dissolved in diethyl ether (400 ml) and treated with 1 N hydrochloric acid in ether (20 ml). A white solid was collected, washed with fresh ether and dried under vacuum at 78° C. giving 7.1 g (91% yield) of benzeneacetamide,3,4-dichloro-N-[1-(3-methoxy phenyl)-1-(1-methyl-2-piperidinyl)methyl]-N-methyl-, hydrochloride.

Anal. Calcd. for $C_{23}H_{28}Cl_2N_2O \cdot HCl \cdot H_2O$: C, 56.39. H, 6.38. N, 5.72. Found: C, 56.46. H, 6.85. N, 6.39.

EXAMPLE 6

Benzeneacetamide,3,4-dichloro-N-((1-(3-hydroxvohenvl)-1-(1-methyl-2-piperidinylmethyl))-N-methyl-,hybdrobromide

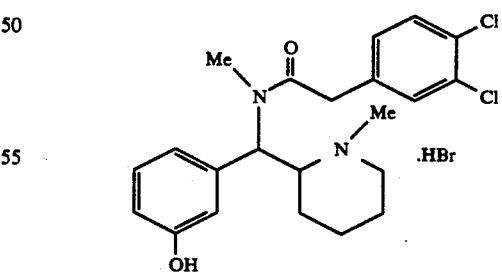

Product from Example 5 (2.0 g, 0.0042 mol) was dissolved in methylene chloride (20 ml) under nitrogen and cooled to −78° C. Boron tribromide (0.021 mol, 1M in methylene chloride) was added dropwise. Stirring was continued at −78° C. for 2 hours before the cooling bath was removed. After the reaction mixture had warmed to ambient temperature while stirring (2.5 hours), the reaction mixture was cooled in an ice bath and water (20 ml) was added dropwise. A white solid was collected and recrystallized in methanol/isopropanol. The resultant white crystals were dried under vacuum at 60° C. giving 1.08 g (51% yield) of benzeneacetamide,3,4-dichloro-N-[1-(3-hydroxyphenyl)-1-(1-methyl-2-piperidinyl)methyl]-N-methyl-, hydrobromide.

Anal. Calcd. for C$_{22}$H$_{26}$Cl$_2$N$_2$O$_2$.HBr.0.5C$_3$H$_8$O: C, 53.02. H, 5.87. N, 5.26. Found: C, 51.56. H, 5.50. N, 5.26.

EXAMPLE 7

Benzeneacetamide, 3,4-dichloro-N-((1-(4-methoxyphenyl)-1-(1-methyl-2-piperidinylmethyl))-N-methyl-, hydrochloride

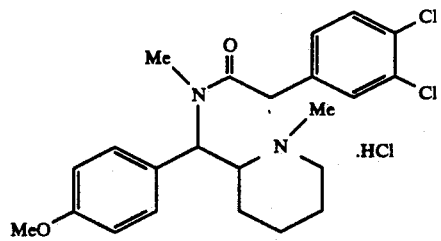

2-Pyridyl-4-methoxyphenyl ketone was prepared according to the procedure given in JOC 16, 1790 (1951). Collected 12.81 g (38% yield) light tan crystals. Subsequent synthetic steps were similar to those given in Example 5.

TABLE 1

| Ex. | Y | R | R$^2$ | R$^3$ | X | Z | m.p. |
|---|---|---|---|---|---|---|---|
| 1 | O | phenyl | Me | 3,4-dichlorophenyl | CH$_2$ | N-methyl-2-pyrrolidinyl | 205–209° C. |
| 2 | O | phenyl | Me | 3,4-dichlorophenyl | CH$_2$ | N-methyl-2-piperidinyl | 240–243° C. |
| 3 | O | phenyl | Me | 3,4-dichlorophenyl | CH$_2$ | N-cyclopropylmethyl 2-piperidinyl | 120–130° C. |
| 4 | O | phenyl | Me | 3,4-dichlorophenyl | CH$_2$ | N-methyl-2-piperidinyl | 185–187° C. |
| 5 | O | 3-methoxyphenyl | Me | 3,4-dichlorophenyl | CH$_2$ | N-methyl-2-piperidinyl | (a) |
| 6 | O | 3-hydroxyphenyl | Me | 3,4-dichlorophenyl | CH$_2$ | N-methyl-2-piperidinyl | 184–187° C. |
| 7 | O | 4-methoxyphenyl | Me | 3,4-dichlorophenyl | CH$_2$ | N-methyl-2-piperidinyl | 203–205° C. |
| 8 | O | 4-hydroxyphenyl | Me | 3,4-dichlorophenyl | CH$_2$ | N-methyl-2-piperidinyl | 153–156° C. |
| 9 | O | phenyl | Me | 3,4-dichlorophenyl | CH$_2$ | N-methyl-2 piperidinyl | 222–224° C. (methane sulfonic acid salt) |
| 10 | O | phenyl | Me | pentafluorophenyl | CH$_2$ | N-methyl-2 piperidinyl | 253–255° C. |
| 11 | O | phenyl | ethyl | 3,4-dichlorophenyl | CH$_2$ | N-methyl-2 piperidinyl | 158–163° C. |
| 12 | O | phenyl | ethyl | 3,4-dichlorophenyl | CH$_2$ | N-methyl-2 piperidinyl | 218–221° C. |
| 13 | O | phenyl | Me | 2,4-dichlorophenyl | CH$_2$ | N-methyl-2 piperidinyl | 243–246° C. |
| 14 | O | phenyl | Me | 3,4-dichlorophenyl | CH$_2$O— | N-methyl-2 piperidinyl | 196–199° C. |
| 15 | O | phenyl | Me | 5-chlorothiopene |  | N-methyl-2 piperidinyl | 225–227° C. |
| 16 | O | phenyl | Me | 3,4-dichloro phenyl | —CH$_2$CH$_2$ | N-methyl-2 piperidinyl | 106–109° C. |
| 18 | O | phenyl | Me | 4-benzo[b]-furanyl | CH$_2$ | N-methyl-2 piperidinyl |  |
| 19 | O | 4-fluorophenyl | Me | 3,4-dichlorophenyl | CH$_2$ | N-methyl-2 piperidinyl |  |
| 20 | O | 2-furanyl | Me | 3,4-dichlorophenyl | CH$_2$ | N-methyl-2 piperidinyl |  |
| 21 | O | 3-furanyl | Me | 3,4-dichlorophenyl | CH$_2$ | N-methyl-2 piperidinyl |  |
| 22 | O | 2-thienyl | Me | 3,4-dichloro phenyl | CH$_2$ | N-methyl-2 piperidinyl |  |
| 23 | O | 3-thienyl | Me | 3,4-dichlorophenyl | CH$_2$ | N-methyl-2 piperidinyl |  |

TABLE 1-continued $$R^2\underset{\underset{Z}{\overset{|}{R}}}{\overset{\overset{Y}{\|}}{N}}-C-X-R^3$$

| Ex. | Y | R | R² | R³ | X | Z | m.p. |
|---|---|---|---|---|---|---|---|
| 24 | O | 4-fluoro-phenyl | Me | 3,4-dichloro-phenyl | CH₂O— | N-methyl-2-piperidinyl | |
| 25 | O | 4-fluoro-phenyl | Me | 4-benzo[b]-furanyl | CH₂ | N-methyl-2-piperidinyl | |
| 26 | O | 3-methoxy-phenyl | Me | 3,4-dichloro-phenyl | CH₂O— | N-methyl-2-piperidinyl | |
| 27 | O | 3-methoxy-phenyl | Me | 4-benzo[b]-furanyl | CH₂ | N-methyl-2-piperidinyl | |
| 28 | O | 3-hydroxy-phenyl | Me | 3,4-dichloro-phenyl | CH₂O— | N-methyl-2-piperidinyl | |
| 29 | O | 3-hydroxy-phenyl | Me | 4-benzo[b]-furanyl | CH₂ | N-methyl-2-piperidinyl | |
| 30 | O | 4-methoxy-phenyl | Me | 3,4-dichloro-phenyl | CH₂O— | N-methyl-2-piperidinyl | |
| 31 | O | 4-methoxy-phenyl | Me | 4-benzo[b]-furanyl | CH₂ | N-methyl-2-piperidinyl | |
| 32 | O | 4-hydroxy-phenyl | Me | 3,4-dichloro-phenyl | CH₂O | N-methyl-2-piperidinyl | |
| 33 | O | 4-hydroxy-phenyl | Me | 4-benzo[b]-furanyl | CH₂ | N-methyl-2-piperidinyl | |
| 34 | O | 2-furanyl | Me | 3,4-dichloro-phenyl | CH₂O— | N-methyl-2-piperidinyl | |
| 35 | O | 2-furanyl | Me | 4-benzo[b]-furanyl | CH₂ | N-methyl-2-piperidinyl | |
| 36 | O | 3-furanyl | Me | 3,4-dichloro-phenyl | CH₂O— | N-methyl-2-piperidinyl | |
| 37 | O | 3-furanyl | Me | 4-benzo[b]-furanyl | CH₂ | N-methyl-2-piperidinyl | |
| 38 | O | 2-thienyl | Me | 3,4-dichloro-phenyl | CH₂O | N-methyl-2-piperidinyl | |
| 39 | O | 2-thienyl | Me | 4-benzo[b]furanyl | CH₂ | N-methyl-2-piperidinyl | |
| 40 | O | 3-thienyl | Me | 3,4-dichloro-phenyl | CH₂O | N-methyl-2-piperidinyl | |
| 41 | O | 3-thienyl | Me | 4-benzo[b]-furanyl | CH₂ | N-methyl-2-piperidinyl | |
| 42 | O | 3,4-dimethoxy-phenyl | Me | 3,4-dichloro-phenyl | CH₂ | N-methyl-2-piperidinyl | |
| 43 | O | 3-nitrophenyl | Me | 3,4-dichloro-phenyl | CH₂ | N-methyl-2-piperidinyl | |
| 44 | O | 4-biphenyl | Me | 3,4-dichloro-phenyl | CH₂ | N-methyl-2-piperidinyl | |
| 45 | O | 2-napthyl | Me | 3,4-dichloro-phenyl | CH₂ | N-methyl-2-piperidinyl | |
| 46 | O | ethyl | Me | 3,4-dichloro-phenyl | CH₂ | N-methyl-2-piperidinyl | |
| 47 | O | benzyl | Me | 3,4-dichloro-phenyl | CH₂ | N-methyl-2-piperidinyl | 96-99° C. |
| 48 | O | phenyl | Me | 3,4-dichloro-phenyl | CH₂ | N-methyl-2-piperidinyl | |
| 49 | O | phenyl | Me | 3,4-dichloro-phenyl | CH₂ | N-methyl-2-piperidinyl | |
| 50 | O | phenyl | Me | 3,4-dichloro-phenyl | CH₂ | N-methyl-2-piperidinyl | |
| 51 | O | phenyl | Me | 3,4-dichloro-phenyl | CH₂S— | N-methyl-2-piperidinyl | |
| 52 | O | phenyl | Me | 4-benzo[b]-thiophene | CH₂ | N-methyl-2-piperidinyl | |
| 53 | O | phenyl | Me | 4-CF₃-phenyl | CH₂ | N-methyl-2-piperidinyl | |
| 54 | O | phenyl | Me | 3,4-dichloro-phenyl | CH₂O— | N-methyl-2-pyrrolidinyl | |
| 55 | O | phenyl | Me | 4-benzo[b]-thiophene | CH₂O— | N-methyl-2-pyrrolidinyl | |
| 56 | O | phenyl | Me | 4-benzo[b]-furanyl | CH₂O | N-methyl-2-pyrrolidinyl | |
| 57 | O | phenyl | Me | 3,4-dichloro-phenyl | CH₂S— | N-methyl-2-pyrrolidinyl | |
| 58 | O | phenyl | Me | 3,4-dichloro-phenyl | CH₂NH— | N-methyl-2-pyrrolidinyl | |
| 59 | O | phenyl | Me | 4-benzo[b]-thiophene | CH₂NH— | N-methyl-2-piperidinyl | |
| 60 | O | phenyl | Me | 4-benzo[b]-furanyl | CH₂NH— | N-methyl-2-piperidinyl | |

TABLE 1-continued $$R^2\text{-}N(\text{R,Z})\text{-}C(=Y)\text{-}X\text{-}R^3$$

| Ex. | Y | R | R² | R³ | X | Z | m.p. |
|---|---|---|---|---|---|---|---|
| 61 | O | phenyl | Me | 3,4-dichlorophenyl | CH₂NH— | N-methyl-2-piperidinyl | |
| 62 | O | phenyl | Me | 4-benzo[b]thiophene | CH₂S— | N-methyl-2-piperidinyl | |
| 63 | O | phenyl | Me | 4-benzo[b]furanyl | CH₂S— | N-methyl-2-piperidinyl | |
| 64 | O | phenyl | Me | 4-benzo[b]thiophene | CH₂S— | N-methyl-2-pyrrolidinyl | |
| 65 | O | phenyl | Me | 4-benzo[b]furanyl | CH₂S— | N-methyl-2-pyrrolidinyl | |
| 66 | O | phenyl | Me | 3,4-dichlorophenyl | CH₂O— | N-allyl-2-piperidinyl | |
| 67 | O | phenyl | Me | 3,4-dichlorophenyl | CH₂ | N-allyl-2-pyrrolidinyl | |
| 68 | O | phenyl | Me | 3,4-dichlorophenyl | CH₂O— | N-allyl-2-pyrrolidinyl | |
| 69 | O | phenyl | Me | 3,4-dinitrophenyl | CH₂O | N-methyl-2-piperidinyl | |
| 70 | O | phenyl | Me | pentafluorophenyl | CH₂O— | N-methyl-2-piperidinyl | |
| 71 | O | phenyl | Me | 3,4-dichlorophenyl | CH₂ | N-methyl-2-pentahydroazepine | |
| 72 | O | phenyl | Me | 3,4-dichlorophenyl | CH₂O— | N-methyl-2-pentahydroazepine | |
| 73 | O | phenyl | Me | 3,4-dichlorophenyl | CH₂NH | N-methyl-2-pentahydroazepine | |
| 74 | O | phenyl | Me | 3,4-dichlorophenyl | CH₂S— | N-methyl-2-pentahydroazepine | |
| 75 | O | phenyl | Me | 3,4-dichlorophenyl | CH₂ | N-methyl-2-hexahydroazocine | |
| 76 | O | phenyl | Me | 3,4-dichlorophenyl | CH₂O— | N-methyl-2-hexahydroazocine | |
| 77 | O | phenyl | Me | 3,4-dichlorophenyl | CH₂NH— | N-methyl-2-hexahydroazocine | |
| 78 | O | phenyl | Me | 3,4-dichlorophenyl | CH₂S— | N-methyl-2-hexahydroazocine | |
| 79 | O | phenyl | Me | pentafluorophenyl | CH₂O— | N-methyl-2-hexahydroazocine | |
| 80 | O | phenyl | Me | pentafluorophenyl | CH₂O— | N-methyl-2-pentahydroazepine | |
| 81 | O | phenyl | Me | 4-benzo[b]furanyl | CH₂ | N-methyl-2-pentahydroazepine | |
| 82 | O | phenyl | Me | 4-benzo[b]furanyl | CH₂ | N-methyl-2-hexahydroazocine | |
| 83 | O | phenyl | Me | 4-benzo[b]thiophene | CH₂ | N-methyl-2-pentahydroazepine | |
| 84 | O | phenyl | Me | 4-benzo[b]thiophene | CH₂ | N-methyl-2-hexahydroazocine | |
| 85 | S | phenyl | Me | 3,4-dichlorophenyl | CH₂ | N-methyl-2-piperidinyl | |
| 86 | S | phenyl | Me | 3,4-dichlorophenyl | CH₂O— | N-methyl-2-piperidinyl | |
| 87 | S | phenyl | Me | 3,4-dichlorophenyl | CH₂ | N-methyl-2-pyrrolidinyl | |
| 88 | S | phenyl | Me | 3,4-dichlorophenyl | CH₂O— | N-methyl-2-pyrrolidinyl | |
| 89 | S | phenyl | Me | 3,4-dichlorophenyl | CH₂O— | N-methyl-2-pentahydroazepine | |
| 90 | S | phenyl | Me | 3,4-dichlorophenyl | CH₂O— | N-methyl-2-hexahydroazocine | |
| 91 | O | phenyl | Me | 3,4-dichlorophenyl | CH₂ | N-methyl-3-pyrrolidinyl | |
| 92 | O | phenyl | Me | 3,4-dichlorophenyl | CH₂O— | N-methyl-3-pyrrolidinyl | |
| 93 | O | phenyl | Me | 3,4-dichlorophenyl | CH₂ | N-methyl-3-piperidinyl | |
| 94 | O | phenyl | Me | 3,4-dichlorophenyl | CH₂O— | N-methyl-3-piperidinyl | |
| 95 | O | phenyl | Me | 3,4-dichlorophenyl | CH₂ | N-methyl-4-piperidinyl | |
| 96 | O | phenyl | Me | 3,4-dichlorophenyl | CH₂O— | N-methyl-4-piperidinyl | |
| 97 | O | phenyl | Me | 3,4-dichlorophenyl | CH₂O— | N-methyl-3-pentahydroazepine | |

TABLE 1-continued $$R^2\diagdown_{N}\diagup^{Y}_{\diagdown X-R^3}$$
$$R\diagup \diagdown Z$$

| Ex. | Y | R | $R^2$ | $R^3$ | X | Z | m.p. |
|---|---|---|---|---|---|---|---|
| 98 | O | phenyl | Me | 3,4-dichloro-phenyl | $CH_2O-$ | N-methyl-4-pentahydroazepine | |
| 99 | O | phenyl | Me | 3,4-dichloro-phenyl | $CH_2O-$ | N-methyl-5-pentahydroazepine | |
| 100 | O | phenyl | Me | 3,4-dichloro-phenyl | $CH_2O-$ | N-methyl-3-hexahydroazocine | |
| 101 | O | phenyl | Me | 3,4-dichloro-phenyl | $CH_2O-$ | N-methyl-4-hexahydroazocine | |
| 102 | O | phenyl | Me | 3,4-dichloro-phenyl | $CH_2O-$ | N-methyl-5-hexahydroazocine | |
| 103 | O | phenyl | Me | 3,4-dichloro-phenyl | $CH_2O-$ | N-methyl-6-hexahydroazocine | |
| 104 | O | phenyl | Me | 3,4-dichloro-phenyl | $CH_2-$ | N-methyl-3-pentahydroazepine | |
| 105 | O | phenyl | Me | 3,4-dichloro-phenyl | $CH_2-$ | N-methyl-3-hexahydroazocine | |

(a) Anal. Calcd. for $C_{23}H_{28}Cl_2N_2O_2 \cdot HCl \cdot H_2O$: C, 56.39. H, 6.38. N, 5.72. Found: C, 56.46. H, 6.85. N, 6.39.

The following examples were prepared as described in Scheme 2 of this application.

EXAMPLE 106

(+)-[2S-(R*,R*)]-(3,4-dichlorophenyl)-N-methyl-N-[1-(1-methyl -2-piperidinyl)phenyl methyl]acetamide hydrochloride (Compound of Formula (VII) of Scheme 2

To a solution of 3,4-dichlorophenylacetic acid (0.58 g, 2.8 mmol) in dry THF (10 ml) under $N_2$ was added with stirring 1,1-carbonyl-diimidazole (0.46 g, 2.8 mmol). The solution was stirred for 50 minutes at room temperature and then cooled in an ice/water bath. A solution of (S,S)-N-methyl-N-1-(1-methyl-2-piperidinyl) phenyl methylamine (0.52 g, 2.4 mmol) in dry THF (5 ml) was added dropwise. The solution was allowed to slowly warm to room temperature and was stirred overnight. The solvent was then evaporated in vacuo. The residue was dissolved in ether (200 ml) and the solution washed with 1N NaOH (50 ml), water, saturated brine, dried over $Na_2SO_4$ and evaporated. The residue was chromatographed on silica eluting with ethyl acetate saturated with ammonium hydroxide. The residue was dissolved in methylene chloride and the solution was washed with water, saturated brine, dried over $Na_2SO_4$, and evaporated. The residue was dissolved in ether and treated with HCl in ether. The mixture was filtered and the recovered solid recrystallized from acetone. Recovered 0.52 g (49%) of a white solid; $[\alpha]^{25} = 116.7°$ (c=0.32, MeOH).

Preparation of Intermediates as described in Scheme 2
(+)-2S-(R*,R*)1-N-1-dimethyl -alpha-phenpl-2-piperidine methanamine (Preparation of Compound of Formula (VI) of Scheme 2)

To a solution of (+)-(1 S,2S)-N-1-(methyl-2-piperidinyl)-1-phenyl methanol (997 mg, 4.86 mmol) methylene chloride (16 ml) under N2 cooled in an ice/water bath with stirring was added triethylamine (0.81 ml, 5.83 mmol) followed by dropwise addition of methanesulfonyl chloride (0.41 ml, 5.34 mmol) in methylene chloride (4 ml). The reaction was stirred at 0° C. for 30 minutes then allowed to warm to room temperature.

After 3 hours the solvent was removed in vacuo at room temperature or below. The residue was refluxed in 33% methylamine in ethanol (100 ml) with stirring overnight. The solvent was removed in vacuo and the residue was partitioned between saturated sodium bicarbonate and methylene chloride. The organic extract was dried over sodium sulfate and the solvent removed. The residue was distilled bulb to bulb (60°-80° C., 20 mT) to give 990 mg of an oil (93%); $[\alpha]^{25}b = +49.17°$ (c=0.606, $CHCl_3$).

(+)-[2S-(R*, R*)]-1-methyl-alpha-phenyl-2-piperidine-methanol (Preparation of Compound of Formula (V) of Scheme 2)

A solution of (+)-(1 S,2S)-2-piperidinyl-1-phenylmethanol (1.58 g, 8.26 mmol) in 88% formic acid ml) and 37% aqueous formaldehyde (6 ml) was heated to 95° C. with stirring overnight. The solvent was removed in vacuo and the residue was partitioned between methylene chloride and 10% aqueous sodium hydroxide. The aqueous layer was extracted with methylene chloride (3×) and the combined organic extracts were dried over $Na_2SO_4$ and evaporated. The residue was distilled bulb to bulb (80°-100° C., 20 mT) to give 1.05 g of a white solid (62%). An analytical sample was prepared by recrystallization from hexanes, mp 61.6°-62.6° C., $[\alpha]^{25} = +33.4°$ (c=0.608, $CHCl_3$).

TABLE 2

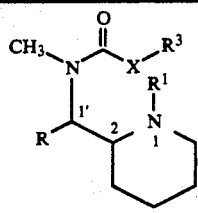

| Ex# | R | R¹ | X | R³ | Absolute Stereochem 1' | 2 | $[\alpha]^D$ |
|---|---|---|---|---|---|---|---|
| 106 | phenyl | CH₃ | CH₂ | 3,4 di-Cl phenyl | S | S | +116.66° |
| 107 | phenyl | CH₃ | CH₂ | 3,4 di-Cl phenyl | R | R | −99.14° |
| 109 | phenyl | CH₃ | CH₂ | 3,4 di-Cl phenyl | R | S | −124.01° |
| 110 | phenyl | CH₃ | CH₂—O— | 3,4 di-Cl phenyl | S | S | +104.62° |
| 111 | phenyl | CH₃ | CH₂—O— | 3,4 di-Cl phenyl | R | R | +103.96° |
| 112 | phenyl | CH₃ | CH₂—O— | 3,4 di-Cl phenyl | S | R | +161.26° |
| 113 | phenyl | CH₃ | CH₂—O— | 3,4 di-Cl phenyl | R | S | −161.51° |
| 114 | phenyl | CH₃ | CH₂ | 4-benzo[b]-furanyl | S | S | +79.80 |
| 115 | phenyl | CH₃ | CH₂ | 4-benzo[b]-furanyl | R | R | |
| 116 | phenyl | CH₃ | CH₂ | 4-benzo[b]-furanyl | S | R | |
| 117 | phenyl | CH₃ | CH₂ | 4-benzo[b]-furanyl | R | S | |
| 118 | 4-fluoro phenyl | CH₃ | CH₂ | 3,4 di-Cl phenyl | S | S | +103.67 |
| 119 | 4-fluoro phenyl | CH₃ | CH₂ | 3,4 di-Cl phenyl | R | R | |
| 120 | 3-methoxy phenyl | CH₃ | CH₂ | 3,4 di-Cl phenyl | S | S | +101.77 |
| 121 | 3-methoxy phenyl | CH₃ | CH₂ | 3,4 di-Cl phenyl | R | R | |
| 122 | 3-hydroxy phenyl | CH₃ | CH₂ | 3,4 di-Cl phenyl | S | S | +68.05 |
| 123 | 3-hydroxy phenyl | CH₃ | CH₂ | 3,4 di-Cl phenyl | R | R | |
| 124 | 4-methoxy phenyl | CH₃ | CH₂ | 3,4 di-Cl phenyl | S | S | |
| 125 | 4-methoxy phenyl | CH₃ | CH₂ | 3,4 di-Cl phenyl | R | R | |
| 126 | 4-hydroxy phenyl | CH₃ | CH₂ | 3,4 di-Cl phenyl | S | S | |
| 127 | 4-hydroxy phenyl | CH₃ | CH₂ | 3,4 di-Cl phenyl | R | R | |
| 128 | 2-furanyl | CH₃ | CH₂ | 3,4 di-Cl phenyl | S | S | |
| 129 | 2-furanyl | CH₃ | CH₂ | 3,4 di-Cl phenyl | R | R | |
| 130 | 3-furanyl | CH₃ | CH₂ | 3,4 di-Cl phenyl | S | S | |
| 131 | 3-furanyl | CH₃ | CH₂ | 3,4 di-Cl phenyl | R | R | |
| 132 | 2-thienyl | CH₃ | CH₂ | 3,4 di-Cl phenyl | S | S | |
| 133 | 2-thienyl | CH₃ | CH₂ | 3,4 di-Cl phenyl | R | R | |
| 134 | 3-thienyl | CH₃ | CH₂ | 3,4 di-Cl phenyl | S | S | |
| 135 | 3-thienyl | CH₃ | CH₂ | 3,4 di-Cl phenyl | R | R | |
| 136 | 4-fluoro phenyl | CH₃ | CH₂—O— | 3,4 di-Cl phenyl | S | S | +117.97 |
| 137 | 4-fluoro phenyl | CH₃ | CH₂ | 3,4 di-Cl phenyl | R | R | |
| 138 | 4-fluoro phenyl | CH₃ | CH₂ | 4-benzo[b]-furanyl | S | S | |
| 139 | 4-fluoro phenyl | CH₃ | CH₂ | 4-benzo[b]-furanyl | R | R | |
| 140 | 3-methoxy phenyl | CH₃ | CH₂—O— | 3,4 di-Cl phenyl | S | S | +128.52 |
| 141 | 3-methoxy phenyl | CH₃ | CH₂—O— | 3,4 di-Cl phenyl | R | R | |
| 142 | 3-methoxy | CH₃ | CH₂ | 4-benzo[b]- | S | S | |

TABLE 2-continued

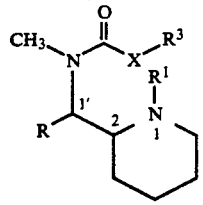

| Ex# | R | R¹ | X | R³ | Absolute Stereochem 1' | 2 | $[\alpha]^D$ |
|---|---|---|---|---|---|---|---|
| | phenyl | | | furanyl | | | |
| 143 | 3-methoxy phenyl | CH₃ | CH₂ | 4-benzo[b]-furanyl | R | R | |
| 144 | 3-hydroxy phenyl | CH₃ | CH₂—O— | 3,4 di-Cl phenyl | S | S | +108.13 |
| 145 | 3-hydroxy phenyl | CH₃ | CH₂—O— | 3,4 di-Cl phenyl | R | R | |
| 146 | 3-hydroxy phenyl | CH₃ | CH₂ | 4-benzo[b]-furanyl | S | S | |
| 147 | 3-hydroxy phenyl | CH₃ | CH₂ | 4-benzo[b]-furanyl | R | R | |
| 148 | 4-methoxy phenyl | CH₃ | CH₂—O— | 3,4 di-Cl phenyl | S | S | |
| 149 | 4-methoxy phenyl | CH₃ | CH₂—O— | 3,4 di-Cl phenyl | R | R | |
| 150 | 4-methoxy phenyl | CH₃ | CH₂ | 4-benzo[b]-furanyl | S | S | |
| 151 | 4-methoxy phenyl | CH₃ | CH₂ | 4-benzo[b]-furanyl | R | R | |
| 152 | 4-hydroxy phenyl | CH₃ | CH₂—O— | 3,4 di-Cl phenyl | S | S | |
| 153 | 4-hydroxy phenyl | CH₃ | CH₂—O— | 3,4 di-Cl phenyl | R | R | |
| 154 | 4-hydroxy phenyl | CH₃ | CH₂ | 4-benzo[b]-furanyl | S | S | |
| 155 | 4-hydroxy phenyl | CH₃ | CH₂ | 4-benzo[b]-furanyl | R | R | |
| 156 | 2-furanyl | CH₃ | CH₂—O— | 3,4 di-Cl phenyl | S | S | |
| 157 | 2-furanyl | CH₃ | CH₂—O— | 3,4 di-Cl phenyl | R | R | |
| 158 | 2-furanyl | CH₃ | CH₂ | 4-benzo[b]-furanyl | S | S | |
| 159 | 2-furanyl | CH₃ | CH₂ | 4-benzo[b]-furanyl | R | R | |
| 160 | 3-furanyl | CH₃ | CH₂—O— | 3,4 di-Cl phenyl | S | S | |
| 161 | 3-furanyl | CH₃ | CH₂—O— | 3,4 di-Cl phenyl | R | R | |
| 162 | 3-furanyl | CH₃ | CH₂ | 4-benzo[b]-furanyl | S | S | |
| 163 | 3-furanyl | CH₃ | CH₂ | 4-benzo[b]-furanyl | S | S | |
| 164 | 2-thienyl | CH₃ | CH₂—O— | 3,4 di-Cl phenyl | S | S | |
| 165 | 2-thienyl | CH₃ | CH₂—O— | 3,4 di-Cl phenyl | R | R | |
| 166 | 2-thienyl | CH₃ | CH₂ | 4-benzo[b]-furanyl | S | S | |
| 167 | 2-thienyl | CH₃ | CH₂ | 4-benzo[b]-furanyl | R | R | |
| 168 | 3-thienyl | CH₃ | CH₂—O— | 3,4 di-Cl phenyl | S | S | |
| 169 | 3-thienyl | CH₃ | CH₂—O— | 3,4 di-Cl phenyl | R | R | |
| 170 | 3-thienyl | CH₃ | CH₂ | 4-benzo[b]-furanyl | S | S | |
| 171 | 3-thienyl | CH₃ | CH₂ | 4-benzo[b]-furanyl | R | R | |
| 172 | 3,4 dimethoxy phenyl | CH₃ | CH₂ | 3,4 di-Cl phenyl | S | S | |
| 173 | 3-nitro phenyl | CH₃ | CH₂ | 3,4 di-Cl phenyl | R | R | |
| 174 | 4-biphenyl | CH₃ | CH₂ | 3,4 di-Cl phenyl | S | S | |
| 175 | 2-naphthyl | CH₃ | CH₂ | 3,4 di-Cl | S | S | |
| 176 | ethyl | CH₃ | CH₂ | 3,4 di-Cl | R | R | |

TABLE 2-continued

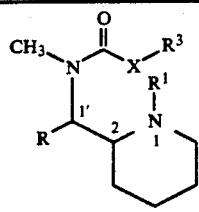

| Ex# | R | R¹ | X | R³ | Absolute Stereochem 1' | 2 | $[\alpha]^D$ |
|---|---|---|---|---|---|---|---|
| 177 | cyclohexyl | CH₃ | CH₂ | 3,4 di-Cl phenyl | S | S | |
| 178 | benzyl | CH₃ | CH₂ | 3,4 di-Cl phenyl | S | S | |
| 179 | phenyl | cyclopropylmethyl | CH₂ | 3,4 di-Cl phenyl | S | S | +89.61 |
| 180 | phenyl | allyl | CH₂ | 3,4 di-Cl phenyl | S | S | +96.01 |
| 181 | phenyl | iPr | CH₂ | 3,4 di-Cl phenyl | S | S | |
| 182 | phenyl | CH₃ | CH₂—S— | 3,4 di-Cl phenyl | S | S | |
| 183 | phenyl | CH₃ | CH₂ | 4-benzo[b]-thiophene | S | S | |
| 184 | phenyl | CH₃ | CH₂ | 4-CF₃ phenyl | S | S | |
| 185 | phenyl | CH₃ | CH₂ | pentafluoro phenyl | S | S | |

Analgesia Testing Procedure

The standard procedure for detecting and comparing the analgesic activity of compounds is the phenylquinone writhing test (PQW) modified from E. Seigmund, et al.; Proc. Soc. Exp. Biol. Med., 95, 729 (1957).

Test compounds were dissolved in saline or distilled water using dilute lactic acid as needed, or suspended in an aqueous vehicle containing 2% by volume of Tween 80 ®, a pharmacological dispersant manufactured by Fisher-Scientific Company and containing 100% polysorbate 80 and 0.25% by weight of Methocel ® A15C powder, a suspending agent manufactured by Dow Chemical company and containing 100% methylcellulose. Test compounds were given orally or subcutaneously to fasted (17–21 hours) male white mice (CF1), 5–15 animals per graded dose, in a volume of 10 ml/kg body weight. After 5–25 minutes, aqueous 0.01% phenyl-p-benzoquinone, 0.125 mg/kg, was injected intraperitoneally. After an additional 5 minutes, mice were observed 10 minutes for the characteristic stretching or writhing syndrome which is indicative of pain produced by phenylquinone. The effective analgesic dose in 50% of the mice (ED₅₀) was calculated by the moving average method of W. R. Thompson, Bac. Rev., 11, 115–145 (1947).

The mouse analgesic data are summarized in Table 3.

TABLE 3

| | Analgesic Activity in Mice | |
|---|---|---|
| | MOUSE PQW ED₅₀ | |
| | | (mg/kg) |
| Example No. | s.c. | p.o. |
| 2 | 1.7 | 10. |
| 3 | >81.0 | 47. |
| 5 | 1.3 | 38. |
| 6 | 18.0 | >81. |

TABLE 3-continued

| | Analgesic Activity in Mice | |
|---|---|---|
| | MOUSE PQW ED₅₀ | |
| | | (mg/kg) |
| Example No. | s.c. | p.o. |
| 10 | 16.0 | 47. |
| 9 | 0.72 | 16. |
| 4 | 67.0 | >81. |
| 7 | >81.0 | >81. |
| 8 | >81.0 | >81. |
| 11 | 30.0 | 38. |
| 12 | 1.7 | 24. |
| 13 | 8.1 | 24. |
| 14 | 0.11 | 1.2 |
| 15 | 10.0 | 67. |
| 47 | >81.0 | >81. |
| 107 | 13.0 | 30. |
| 106 | 0.37 | 8.1 |
| 109 | >81.0 | >81. |
| 111 | 1.3 | 19. |
| 110 | 0.078 | 0.89 |
| 113 | 67.0 | >81. |
| 112 | 12.0 | >81. |
| 114 | 0.57 | 8.1 |
| 118 | 1.7 | 19. |
| 120 | 1.6 | 19. |
| 122 | 36. | 47. |
| 136 | 0.24 | 1.7 |
| 140 | 0.29 | 5.2 |
| 144 | 4.2 | 16. |
| 179 | >81.0 | 10. |
| 180 | >81.0 | 24. |

As shown in Table 3, compounds of the invention produce potent analgesic effects in warm-blooded animals. This analgesia is in the same range of potency as morphine and of the standard kappa agonist analgesic U-50,488H [P. F. VonVoigtlander, et al.; J. Pharmacol. Exp. Ther., 224, 7 (1983)].

Strong sedation, occurring at ≧3x the analgesic ED50 dose, was an additional property observed with all compounds of the invention when tested in mice. This sedation is characteristic of kappa agonist compounds such as U-50,488H [P. F. VonVoigtlander, et al.; J. Pharmacol. Exp. Ther., 224, 7 (1983)]. Morphine and other mu agonist compounds do not produce sedation in mice. All compounds of the invention which produced analgesia in mice (Table 3) also produced strong sedation within their analgesically-effective range of doses, suggesting that they have selective kappa agonist activity.

METHODS

Opioid Receptor Binding

Male Hartley guinea pigs (250-300 g, Charles River) were sacrificed by decapitation. Brain membranes were prepared by the method of Tam (S. W. Tam, Proc. Natl. Acad. Sci. USA 80, 6703-6707, (1983). Whole brains were homogenized (20 sec) in 10 vol (wt/vol) of ice-cold 0.34 M sucrose with a Brinkmann Polytron (setting 8). The homogenate was centrifuged at 920×g for 10 min. The supernatant was centrifuged at 47,000×g for 20 min. The resulting membrane pellet was resuspended in 10 vol (original wt/vol) of 50 mM Tris HCl (pH 7.4) and incubated at 37° C. for 45 minutes to degrade and dissociate bound endogenous ligands. The membranes were then centrifuged at 47,000×g for 20 min and resuspended in 50 mM Tris HCl (50 ml per brain). Opioid receptor binding assays were performed according to the method of S. W. Tam, Eur. J. Pharmacol. 109, 33-41, 1985. 0.5 ml aliquots of the membrane preparation were incubated with unlabeled drugs, labeled ligands, 50 mM Tris HCl containing NaCl (100 mM), pH 7.4, in a final volume of 1 ml. After 45 min of incubation at room temperature, samples were filtered rapidly through Whatman GF/C glass filters under negative pressure, and washed three times with ice-cold Tris HCl (5 ml).

Labeled ligands were used at the following final concentrations: 0.5 nM [3H]naloxone (mu binding); 1 nM (−)-[$^3$H]ethylketocycloazocine (EKC) in the presence of 500 nM [D-Ala$^2$-D-Leu$^5$]enkephalin (DADLE) and 20 nM sufentanil (kappa binding) and 1.0 nM [$^3$H]DADLE in the presence of a 4 nM sufentanil (delta binding). Under these experimental conditions, the apparent Kds for naloxone, (-)-[3H]EKC and [3H]DADLE were 0.98, 0.62 and 0.64 nM, respectively. Nonspecific binding of [$^3$H]naloxone, (−)-[$^3$H]EKC and [3H]DADLE were determined in the presence of 10 μM naloxone, (±) EKC and naloxone, respectively.

IC$_{50}$s were calculated from log-logit plots. Apparent K$_i$s were calculated from the equation, $K_i = IC_{50}/[1+(L/K_d)]$, where L is the concentration of radioligand and K$_d$ is its dissociation constant (Y. C. Cheng and W. H. Pursoff, Biochem. Pharm. 22: 3099-3108, 1973).

TABLE 4

| | Opioid Receptor Binding in Rat Brain Homogenates | |
|---|---|---|
| | Receptor Binding Ki (nM) | |
| Example No. | KAPPA | MU |
| 2 | 7 | 270 |
| 3 | 530 | 957 |
| 5 | 152 | 3470 |
| 6 | 9 | 438 |
| 10 | 57 | 3200 |
| 9 | 8 | 322 |
| 4 | 1283 | 28515 |
| 7 | 4586 | 5668 |
| 8 | 2590 | 11360 |

TABLE 4-continued

| | Opioid Receptor Binding in Rat Brain Homogenates | |
|---|---|---|
| | Receptor Binding Ki (nM) | |
| Example No. | KAPPA | MU |
| 11 | 20 | 660 |
| 12 | 19 | 3325 |
| 13 | 19 | 625 |
| 14 | 7 | 58 |
| 15 | 12400 | 8700 |
| 47 | 3995 | 2555 |
| 107 | 42 | 253 |
| 106 | 6 | 414 |
| 109 | 1655 | 3864 |
| 111 | 18 | 195 |
| 110 | 3 | 8 |
| 113 | 2433 | >10000 |
| 112 | 415 | 4616 |
| 114 | 13 | 250 |
| 118 | 7 | 1064 |
| 120 | 17 | 633 |
| 122 | 3 | 209 |
| 136 | 2 | 54 |
| 140 | 14 | 104 |
| 144 | 1 | 27 |
| 179 | 397 | 604 |
| 180 | 46 | 530 |

DOSAGE FORMS

Dosage forms (compositions) suitable for administration contain from about 0.1 milligram to about 500 milligrams of active ingredient per unit. In these pharmaceutical compositions the active ingredient will ordinarily be present in an amount of about 0.5-95% by weight based on total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or entericcoated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of the active ingredient, 3 milligrams of magnesium stearate, 75 milligrams of microcrystalline cellulose, 10 milligrams of starch and 112 milligrams of lactose. Appropriate coatings may be applied to increase palatability or delay absorption.

INJECTABLE COMPOSITION

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The term "consisting essentially of" as used in the present disclosure is intended to have its customary meaning, namely, that all specified specified material and conditions are very important in practicing the invention but that unspecified materials and conditions are not excluded so long as they do not prevent the benefits of the invention from being realized.

What is claimed is:

1. A compound of the formula:

$$\underset{(CH_2)_n}{\overset{Y}{\underset{R}{\overset{\|}{R^2\diagdown N\diagup X-R^3}}}} \quad N-R^1 \quad (I)$$

or a pharmceutically acceptable salt or stereoisomer thereof wherein:

R is C1-C10 alkyl, C6-C10 carbocyclic aromatic ring, $(CH_2)_mOAr$, $(CH_2)_mSAr^1$ (m=1-3), lower alkyl bearing a C6-C10 carbocyclic aromatic ring, each optionally substituted with 1-5 substituents independently selected from the group consisting of:

fluorine, chlorine, bromine, trifluoromethyl, cyano, nitro, hydroxy, thiol, trifluoromethylsulfonyl, 1,1,2,2-tetrafluoroethylsulfonyl, C1-C3 alkyl, C1-C3 alkoxy, haloalkyl of 1-3 carbon atoms and 1-7 halogen atoms, $CO_2H$, tetrazole, carboalkoxy of 2-6 carbon atoms, $S(O)_qR^4$ (q=0-3), $NR^5R^6$, $COR^7$, $CONR^8R^9$ and $SO_2NR^8R^9$;

$R^1$ is H, C1-C6 alkyl, C1-C6 alkenyl including branched chain alkenyl, C3-C6 cycloalkyl, C3-C6 cycloalkylmethyl, benzyl, phenethyl, and 3-phenylpropyl;

$R^2$ is C1-C3 alkyl;

$R^3$ is C6-C10 carbocyclic ring, each optionally substituted with 1-5 substituents independently selected from the group consisting of:

fluorine, chlorine, bromine trifluoromethyl, cyano, nitor, hydroxy, thiol, trifluoromethylsulfonyl, 1,1,2,2-tetrafluoroethylsulfonyl, C1-C3 alkoxy, $CO_2H$, tetrazole, carboalkoxy of 2-6 carbon atoms, $S(O)_qR^4$ (q=0-3), $NR^5R^6$, $COR^7$, $CONR^8R^9$ and $SO_2NR^8R^9$;

$R^4$ to $R^9$ independently are H or C1-C6 alkyl;

X is single bond, $CH_2$, $CH_2O$, $CH_2S$ or $CH_2NH$;

Y is O or S;

n is 1; and

Ar and $Ar^1$ independently are C6-C10 carbocyclic, or C6-C10 aromatic ring, optionally substituted with 1-5 substituents independently selected from the group consisting of:

fluorine, chlorine, bromine, trifluoromethyl, cyano, nitor, hydroxy, thiol, trifluoromethylsulfonyl, 1,1,2,2-tetrafluoroethylsulfonyl, C1-C3 alkyl, C1-C3 alkoxy, $CO_2H$, tetrazoke, carboalkoxy of 2-6 carbon atoms, $S(O)_qR^4$ (q=0-3) $NR^5R^6$, $COR^7$, $CONR^8R^9$ and $SO_2NR^8R^9$.

2. A compound of claim 1 wherein R is a C6-C10 carbocyclic aromatic ring.

3. A compound of claim 1 wherein X is $CH_2$, $CH_2O$, $CH_2S$ or $CH_2NH$.

4. A compound of claim 1 wherein Y is O.

5. A compound of claim 1 wherein the piperidine ring is attached at the 2-position.

6. A compound of claim 1 wherein
R is a C6-C10 carbocyclic aromatic ring,
X is $CH_2$, $CH_2O$, $CH_2S$ or $CH_2NH$;
Y is O;
n is 1; and:
the piperidine ring is attached at the 2-position.

7. A compound of claim 6 which is the RR or SS diastereomer.

8. A compound of claim 6 wherein R is phenyl or substituted phenyl.

9. A compound of claim 6 wherein $R^1$ and $R^2$ are methyl.

10. A compound of claim 6 wherein $R^3$ is 3,4-dichlorophenyl.

11. A compound of claim 6 wherein X is $CH_2$ or $CH_2O$.

12. A compound of claim 6 wherein:
R is pehnyl or substituted phenyl;
$R^1$ and $R^2$ are methyl;
$R^3$ is 3,4-dichloropehnyl or;
X is $CH_2$ or $CH_2O$;
Y is O;
n is 1; and the piperidine ring is attached at the 2-position.

13. A compound of claim 12 which is the RR or SS diastereomer.

14. A compound of claim 13 which is the SS diastereomer.

15. A pharmaceutical composition comprising a pharmaceutically effective amount of a compound of claim 1 and a pharmaceutically acceptable carrier.

16. A pharmaceutical composition comprising a pharmaceutically effective amount of a compound of claim 2 and a pharmaceutically acceptable carrier.

17. A pharmaceutical composition comprising a pharmaceutically effective amount of a compound of claim 3 and a pharmaceutically acceptable carrier.

18. A pharmaceutical composition comprising a pharmaceutically effective amount of a compound of claim 4 and a pharmaceutically acceptable carrier.

19. A pharmaceutical composition comprising a pharmaceutically effective amount of a compound of claim 5 and a pharmaceutically acceptable carrier.

20. A pharmaceutical composition comprising a pharmaceutically effective amount of a compound of claim 6 and a pharmaceutically acceptable carrier.

21. A pharmaceutical composition comprising a harmaceutically effective amount of a compound of claim 7 and a pharmaceutically acceptable carrier.

22. A pharmaceutical composition comprising a pharmaceutically effective amount of a compound of claim 8 and a pharmaceutically acceptable carrier.

23. A pharmaceutical composition comprising a pharmaceutically effective amount of a compound of claim 9 and a pharmaceutically acceptable carrier.

24. A pharmaceutical composition comprising a pharmaceutically effective amount of a compound of claim 10 and a pharmaceutically acceptable carrier.

25. A pharmaceutical composition comprising a pharmaceutically effective amount of a compound of claim 11 and a pharmaceutically acceptable carrier.

26. A pharmaceutical composition comprising a pharmaceutically effective amount of a compound of claim 12 and a pharmaceutically acceptable carrier.

27. A pharmaceutical composition comprising a pharmaceutically effective amount of a compound of claim 1 and a pharmaceutically acceptable carrier.

28. A pharmaceutical composition comprising a pharmaceutically effective amount of a compound of claim 14 and a pharmaceutically acceptable carrier.

29. A method of using a compound of claim 1 as an analgesic, agent comprising administering to a mammal in need of such an agent an effective amount of such a compound.

30. A method of using a compound of claim 2 as an analgesic, agent comprising administering to a mammal in need of such an agent an effective amount of such a compound.

31. A method of using a compound of claim 3 as an analgesic, agent comprising administering to a mammal in need of such an agent an effective amount of such a compound.

32. A method of using a compound of claim 4 as an analgesic, agent comprising administering to a mammal in need of such an agent an effective amount of such a compound.

33. A method of using a compound of claim 5 as an analgesic, agent comprising administering to a mammal in need of such an agent an effective amount of such a compound.

34. A method of using a compound of claim 6 as an analgesic, agent comprising administering to a mammal in need of such an agent an effective amount of such a compound.

35. A method of using a compound of claim 7 as an analgesic, agent comprising administering to a mammal in need of such an agent an effective amount of such a compound.

36. A method of using a compound of claim 8 as an analgesic, agent comprising administering to a mammal in need of such an agent an effective amount of such a compound.

37. A method of using a compound of claim 9 as an analgesic, agent comprising administering to a mammal in need of such an agent an effective amount of such a compound.

38. A method of using a compound of claim 10 as an analgesic, agent comprising administering to a mammal in need of such an agent an effective amount of such a compound.

39. A method of using a compound of claim 11 as an analgesic, agent comprising administering to a mammal in need of such an agent an effective amount of such a compound.

40. A method of using a compound of claim 12 as an analgesic, agent comprising administering to a mammal in need of such an agent an effective amount of such a compound.

41. A method of using a compound of claim 13 as an analgesic, agent comprising administering to a mammal in need of such an agent an effective amount of such a compound.

42. A method of using a compound of claim 14 as an analgesic, agent comprising administering to a mammal in need of such an agent an effective amount of such a compound.

* * * * *